(12) United States Patent
Funamura et al.

(10) Patent No.: US 7,731,155 B2
(45) Date of Patent: Jun. 8, 2010

(54) MALE LUER CONNECTOR

(75) Inventors: Shigeaki Funamura, Fukuroi (JP); Yosuke Sakai, Fukuroi (JP); Ichiro Kitani, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 372 days.

(21) Appl. No.: 12/016,221

(22) Filed: Jan. 18, 2008

(65) Prior Publication Data

US 2008/0183155 A1 Jul. 31, 2008

(30) Foreign Application Priority Data

Jan. 19, 2007 (JP) .............................. 2007-010702

(51) Int. Cl.
- F16K 51/00 (2006.01)
- F16L 29/00 (2006.01)
- F16L 37/28 (2006.01)

(52) U.S. Cl. ................. 251/149.7; 251/149.6; 604/249; 604/905

(58) Field of Classification Search ............... 251/149.1, 251/149.3, 149.6, 149.7; 604/249, 256, 905
See application file for complete search history.

(56) References Cited

U.S. PATENT DOCUMENTS

| | | | | |
|---|---|---|---|---|
| 3,806,086 A | * | 4/1974 | Cloyd | 251/149.7 |
| 5,439,451 A | * | 8/1995 | Collinson et al. | 604/247 |
| 5,533,983 A | | 7/1996 | Haining | |
| 5,549,577 A | * | 8/1996 | Siegel et al. | 604/256 |
| 6,039,302 A | * | 3/2000 | Cote et al. | 251/149.1 |
| 6,113,068 A | * | 9/2000 | Ryan | 251/149.4 |

FOREIGN PATENT DOCUMENTS

| | | |
|---|---|---|
| JP | 05-031180 | 2/1993 |
| WO | 2004060474 A1 | 7/2004 |
| WO | 2006062912 A1 | 6/2006 |
| WO | 2007008511 A2 | 1/2007 |

OTHER PUBLICATIONS

Extended European Search Report issued in Application No. 08100540.7, dated Jun. 2, 2008, 6 pages.

* cited by examiner

*Primary Examiner*—John K Fristoe, Jr.

(57) ABSTRACT

A male luer connector to prevent generation of bacteria and waste of medicinal liquid.

The male luer connector comprises a basal end and a tip end rotatable relative to the basal end; the male luer part is tapered and rotatable within the tip end. The outer peripheral surface of the tip end is decreased from the rear side to the front side; and a stick-like male luer occluding portion is provided within the male luer part which can tightly occlude liquid from the tip end opening of the male luer part. An internal thread portion is provided on the inner peripheral surface of the basal end and an external thread, helically engaged with the internal thread, is provided to the rear end portion of the male lure, whereby the tip end opening can be opened or closed by rotating the tip end relative to the basal end.

7 Claims, 6 Drawing Sheets

MALE LUER CONNECTOR

FIELD OF THE INVENTION

The invention relates to a male luer connector for coupling one tube member with the other tube member by connecting to the one tube member at the tip end and to the other tube member that is coupled with a female luer connector.

BACKGROUND OF THE INVENTION

In conventional practice, a liquid such as a medicinal liquid or blood and the like are supplied to the internal body of a patient by using a plurality of liquid transfusion tubes. In such a case, between the tubes are communicated with each other by using a connecting tool of medical use including a male luer connector and a female luer connector by coupled with the tip end of each of tubes, respectively, comprising the liquid transfusion line and the like (for example, see Japanese Patent Unexamined Publication H05-31180).

The male luer connector included in this connecting tool for medical use comprises a male luer part (communicating pipe) having a luer tapered outer wall being capable of liquid tightly coupling with the inner peripheral surface of the female luer connector; and a lock ring (outer cap) provided on the outer peripheral side of the male luer part, to which a threaded streak being capable of engaging with a threaded streak formed on the outer wall of the female luer connector on the inner peripheral surface. Also, to the rear end portion of the portion of the male luer part opposed to the inner peripheral surface of the female luer connector, a ring like porous member containing a sterilizing agent.

However, in the conventional male luer connector described above, though the generation of bacteria between the male luer part and the inner peripheral surface of the female luer connector can be prevented by the porous member containing the sterilizing agent provided therebetween, such a member for sterilizing is not provided at the tip end opening of the male luer part. Therefore, with the conventional the male luer connector described above, the male luer part is contacted with the outer air because the tip end thereof is opened resulting in leading the generation of bacteria at the tip end opening or the inside of the male luer part when it is not coupled with the female luer connector.

Moreover, when a priming process is carried out by using the conventional male luer connector, in order to completely fill a medicinal liquid within the male luer part, the medicinal liquid is loaded at the tip end opening of the male luer part until the medicinal liquid is spilled out of the tip end opening of the male luer part and, then, the loading is stopped when the medicinal liquid is spilled out. Thus, there is a problem raised that one portion of the medicinal liquid is wasted. Further, at the priming, the medicinal liquid is spilled out of the tip end opening of the male luer part and there is also the problem that bacteria are generated at the portion where the spilled medicinal liquid is attached.

The invention has been made in the light of these problems and the object of the invention is to provide a male luer connector which can prevent the generation of bacteria as well as the waste of the medicinal liquid.

SUMMARY OF THE INVENTION

In one aspect, the present invention is directed to a male luer connector for communicating one tube member with the other tube member by coupling with one tube member and a female luer connector to which the other tube member is connected. The male luer connector comprises a male luer connector body including a basal end connecting part coupled with the one tube member at the rear part thereof and a cylindrical tip end support part forwardly extended from the front part of the basal end connecting part and being capable of displacing relative to the basal end connecting part while the boundary between the basal end connecting part and the tip end support part is liquid tightly sealed. A male luer part having a generally cylindrical shape and comprising a tip end side portion including an outer peripheral surface is provided within the tip end support part so as to slidably moved within it in the axial direction in the condition where the tip end side portion is protruded from the tip end of the tip end support part and the outer peripheral surface of the tip end side portion is tapered from the rear side to the tip end side. Thereby the male luer part is capable of being liquid tightly contacted with the tapered inner peripheral surface. A male luer occluding part is provided in the insides of the male luer connector and the male luer part which can liquid tightly occlude the tip end opening of the male luer part at the tip end thereof. A displacement mechanism for forwardly and backwardly moving the tip end of the male luer occluding part relative to the tip end opening of the male luer part moves the male luer occluding part relative to the male luer part in the axial direction by using the displacement of the tip end support relative to the basal end connecting part.

BRIEF DESCRIPTION OF THE FIGURES

FIG. 11(*a*) is a cross sectional view and FIG. 11(*b*) is a plane view illustrating the positional relationship between the guide hole and the guide projection.

FIG. 12 (*a*) is a cross sectional view and FIG. 12 (*b*) is a plane view illustrating the positional relationship between the guide hole and the guide projection.

FIG. 13 (*a*) is a cross sectional view and FIG. 13 (*b*) is a plane view illustrating the positional relationship between the guide hole and the guide projection.

FIG. 14 (a) is a cross sectional view and FIG. 14 (b) is a plane view illustrating the positional relationship between the guide hole and the guide projection.

DESCRIPTION OF FIGURE NOTATIONS 10, 50 and 80 each represents the male luer connector body;
11, 11a and 11b each represents the tube;
12, 52 and 82 each represents the basal end connecting portion;
13, 53 and 83 each represents the tip end supporting portion;
15 and 85a each represents the internal thread portion;
20, 60 and 90 each represents elastic seal portion;
21 and 61 each represents the stretch hole;
25, 65 and 95 each represents the male luer part;
29a and 69a each represents the tip end opening;
30, 70 and 70c each represents the male luer occluding portion;
31a and 85 each represents the external thread portion;
35, 75 and 75c each represents the lock ring;
37 and 77 each represents the engagement thread portion;
40 represents the female luer connector;
41 represents the thread portion to be engaged;
42 represents the inner peripheral surface; and
A, B and C each represents the male luer connector.

DETAILED DESCRIPTION OF THE INVENTION

Figure 1:
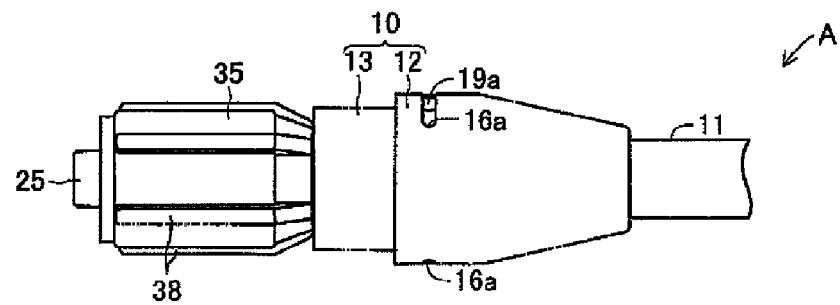
FIG. 1 is a side view illustrating the male luer connector in accordance with the first embodiment of the invention.
Figure 2:
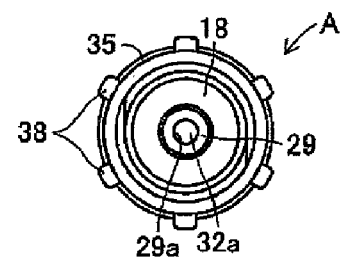
FIG. 2 is a front view illustrating the male luer connector.

The male luer connector of the first embodiment in accordance with the invention will now be explained in detail with the reference to the drawings in below. FIGS. 1 and 2 show a male luer connector A in accordance with the same embodiment. The male luer connector A comprises a male luer connector body 10 formed into a generally cylindrical shape; an elastic seal part 20 provided about the center within the male luer connector 10 as shown in FIGS. 3, 5, 7 and 9; a generally cylindrical male luer part 25 provided from the front side of the elastic seal part 20 within the male luer connector body 10 to the outside of the tip end side of the male luer connector body 10; a stick like male luer occluding part 30 provided within the male luer connector body 10 and the male luer part 25; and a lock ring 35 mounted to the outer periphery of the tip end side of the male luer connector body 10.

The male luer connector body 1—comprises a generally cylindrical basal end connecting part 12 connected to a tube 11 as one of tube members of the invention at the basal end side portion thereof having a diameter gradually increased from the basal end side portion to the tip end side; and a cylindrical tip end supporting part 13 having a step forwardly extended from the tip end portion of the basal end connecting portion 12. Also, the invention will be explained such that the left side represents the front side or the tip end side and the right side represents the rear side or basal end side in FIGS. 1 to 3 and 16 for the male luer connector A, as well as, the left side represents the rear side or basal end side and the right side is front side or tip end side in FIGS. 3 to 16 for the female luer connector 40 as described in below.

Within the basal end connecting portion 12, a flow path 14 for passing a medicinal liquid is formed so as to be a space in which the tip diameter at the end side portion is larger than that at the rear end side portion. Also, between the narrower rear end side portion and the larger tip end side portion in the flow path 14 within the basal end connecting portion 12, a flow path 14a having a diameter slightly greater than that of the rear end side portion and smaller than that at the tip end side portion of the flow path 14 is formed. Further, to the rear side portion of the portion where the flow path 14a is formed in the inner peripheral surface of the basal end connecting portion 12, an internal thread portion 15 is formed and to the front side portion of the portion where the flow path 14a in the inner peripheral surface of the basal end connecting portion 12, a play surface 15a having a smooth curved surface is formed.

Furthermore, at the outer periphery side portion of the narrower portion of the flow path 14 of the rear end side portion of the basal end connecting portion 12, a fixing recess 12a extended toward the tip end side from the rear side portion and opened at the rear end portion is formed along the circumference, in which by engaging the tip end portion of the tube 11 with the fixing recess 12a, the basal end connecting portion 12 is connected to the tube 11. And, at the tip end inner peripheral surface side of the basal end connecting portion 12, an engagement recess 16 extended from the tip end side to the rear side portion of the basal end connecting portion 12 and opened at the tip end portion is formed along the circumference thereof.

To the outer periphery side wall portion of the portion where the engagement recess 16 is formed in the basal end connecting portion 12, a pair of guide holes 16a and 16a are formed such that they maintain the degrees of 180 in the axial direction and penetrate between the outer peripheral surface of the basal end connecting portion 12 and engagement recess 16. The pair of guide holes 16a and 16a are formed into an elongated prolate circle and each extended in the axial direction of the basal end connecting portion 12. Further, the tip end portion of the inner periphery side wall portion of the portion where the engagement recess 16 is formed in the basal end connecting portion 12 is extended to the portion corresponding to the rear end portion of the guide holes 16a and 16a, that is, this inner periphery side wall portion is shorter than the outer periphery side wall portion of the portion where the engagement recess 16 is formed.

The tip end supporting portion 13 comprises a two stepped cylinder connected to the basal end connecting portion 12 to be rotatable in the axial direction, a larger diameter of sliding portion 17 supported by the engagement recess 16 of the basal end connecting portion 12 to be rotatble in the axial direction, and a narrow diameter of supporting portion 18 extended from the tip end center to the front side of the sliding portion 17. To the rear end inner peripheral surface side of the sliding portion 17, a fixing recess 17a extended from the rear end side to the front side portion of the sliding portion 17 and opened at the rear end portion is formed along the circumference. Also, at the outer peripheral surface of the portion where the fixing recess 17a is formed in the sliding portion 17, a pair of guide projections 19a and 19a to be engaged with the guide holes 16a and 16a so as to be moveable within the guide holes 16a and 16a are formed with the distance of the degrees of 180 in the axial direction.

Further, the rear end portion of the inner periphery side wall portion of the portion where the fixing recess 17a is formed, in the sliding portion 17, is extended only to the portion corresponding to the front end portion of the guide projections 19a and 19a, that is, the inner periphery side wall portion is shorter than the outer periphery side wall portion of the portion where the fixing recess 17a is formed. Also, the sliding portion 17 allows the rear end side portion of the outer periphery wall portion to enter the engagement recess 16, whereby it is liquid tightly connected to the basal end connecting portion 12 while the guide projections 19a and 19a are positioned within the corresponding the guide holes 16a and 16a, respectively. And, to the fixing recess 17a, an elastic seal portion 20 is fixed with the periphery edge portion inserted thereinto.

That is to say, the peripheral edge of the elastic seal portion 20 is inserted into the fixing recess 17a to fix the elastic seal portion 20 to the sliding portion 17 and, in that condition, the rear end portion of the sliding portion 17 is attached to the front end portion of the basal end connecting portion 12, whereby the elastic seal portion 20 is contacted to the tip end portion of the inner periphery side wall portion of the portion where the engagement recess 16 is formed to prevent it from being released from the fixing recess 17a. the elastic seal portion 20 comprises a generally disc like rubber having elastic and stretch abilities and is provided with a stretch hole 21 opening or closing by stretching thereof is formed at the center thereof.

Therefore, the elastic seal portion 20 stretches by applying the predetermined pressure force to the front surface thereof to open the stretch hole 21 and constructs by releasing the pressure force to close the stretch hole 21. When the stretch hole 21 is closed, the flow path 14 within the basal end connecting portion 12 is occluded and the medicinal liquid is difficult to flow downstream the elastic seal portion 20. Further, the rear surface of the elastic seal portion 20 is formed into a conical curved surface in which the central side portion is slightly projected toward more rear side than the peripheral edge portion. With the rear surface in which the central side of the elastic seal portion 20 is projected, the pressure applied to the center portion of the elastic seal portion 20 is dispersed as the medicinal liquid is filled within the flow path 14, thereby improving the pressure resistance of the elastic seal portion 20 as well as sealing ability.

The supporting portion 18 is formed into a cylinder being narrower than the sliding portion 17, whereby between the rear end part of the supporting portion 18 in each of the inner and outer peripheral surfaces of the tip end supporting portion 13 and the front end portion of the sliding portion 17, a step is formed, respectively. To the portion except for the tip end side portion in the outer peripheral surface of the supporting portion 18, a recess for sliding 18a having a slightly smaller outer diameter than that of the tip end side portion is formed. Further, within the tip end supporting portion 13, the cylindrical male luer part 25 is attached so as to be slidable in the axial direction. The male luer part 25 comprises a two stepped cylinder having the larger diameter at the rear portion and the narrower diameter at the tip end side, whereby the male luer rear part 26 of the rear side is moveable in the axial direction within the sliding portion 17. Also, the rear side portion of the outer peripheral surface of the male luer rear part 26 is formed to be a tapered surface in which the diameter is decreased as closed to the rear side and the rear end of the male luer rear part 26 is widely opened toward the rear side.

Figure 3:
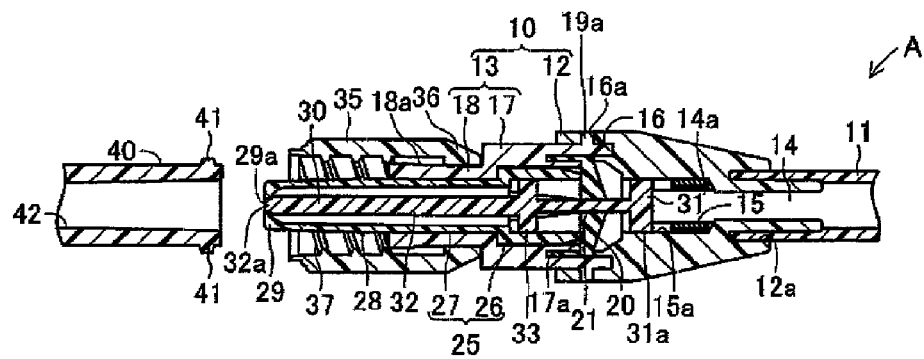
FIG. 3 is a cross sectional view illustrating the condition prior to the male luer connector is connected to the female luer connector.
Figure 4:
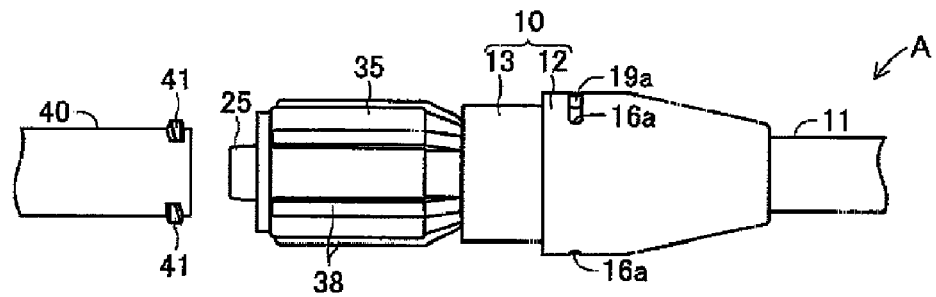
FIG. 4 is a side view illustrating the male luer connector and the female luer connector of FIG. 3.

That is to say, the portion from the front side to the center side of this male luer rear part 26 is formed into a cylinder having a constant outer diameter that is slidably contacted with the inner peripheral surface of the sliding portion 17. The outer diameter of the male luer rear portion 26 is larger than the inner diameter of the supporting portion 18, thereby preventing the male luer rear portion 26 from entering the supporting portion 18. Accordingly, when the male luer part 25 is moved toward the front side within the tip end supporting portion 13, the rear end surface of the male luer rear portion 26 is contacted with the step formed between the rear end portion of the supporting portion 18 and the front end portion of the sliding portion 17 to immobilize the male luer part 25 further toward the front side. FIGS. 3 and 4 show the condition at that time, in this case, the elastic seal portion 20 occludes the rear end opening of the male luer part 25 while being contacted with the rear end surface of the male luer part 25. Also, at that time, the stretch hole 21 of the elastic seal portion 20 is closed.

Figure 5:
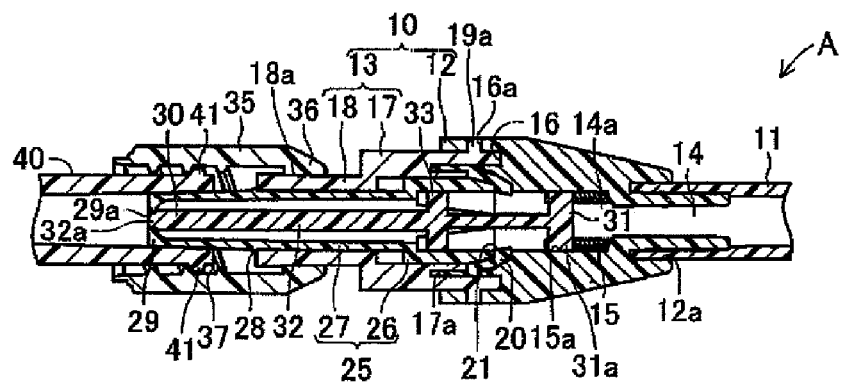
FIG. 5 is a cross sectional view illustrating the male luer connector is being connected to the female luer connector.
Figure 7:
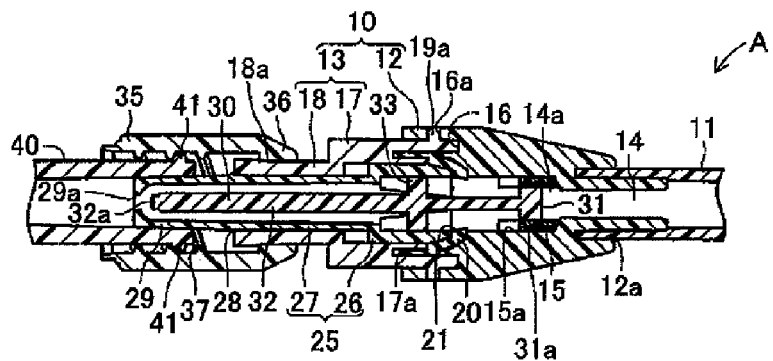
FIG. 7 is a cross sectional view illustrating the condition in which the male luer connector is connected to the female luer connector.

The male luer front portion 27 forming the tip end portion of the male luer part 25 is formed into a cylinder having a taper in which the diameter is gradually decreased from the rear portion side to the tip end side. Further, to the tip end side portion more previous than the center in the front to back direction in the outer peripheral surface of the male luer front portion 27, a small projection 28 is formed along the circumference. Accordingly, when the male luer part 25 is moved toward the rear within the tip end supporting portion 13, as shown in FIGS. 5 and 7, the projection 28 is contacted with the tip end portion of the supporting portion 18, whereby the male luer part 25 can not be moved further toward the rear side of the tip end supporting portion 13. Also, in that condition, the elastic seal portion 20 is pushed to the rear side by the male luer part 25 to open the stretch hole 21. Further, to the tip end portion of the male luer front portion 27, an end surface 29 of smaller diameter is formed and a tip end opening 29a of a small diameter is formed at the center portion thereof.

A male luer occluding portion 30 is provided so as to be moveable in the front to back direction within the male luer connector body 10 and the male luer part 25, and comprises a disc like drive portion 31 formed at the rear end portion, a stick like occluding portion 32 forwardly extended from the front surface of the drive portion 31, and a disc like oscillation preventing portion 33 formed at slightly rear side than the center in the front to back direction in the outer peripheral surface of the occluding portion 32. At the outer peripheral surface of the drive portion 31, an external thread portion 31a that is helically engaged with the internal thread portion 15 of the basal end connecting portion 12, whereby the drive portion 31 is moved in the front to back direction along the internal thread portion 14 by rotating the basal end connecting portion 12 relative to the tip end supporting portion 13 in the axial direction. Also, the drive portion 31 can be freely moved in the axial direction without rotating the inside of the play surface 15a formed to the inner surface of the basal end connecting portion 12.

To the tip end portion of the occluding portion 32, a plug 32a having a narrow diameter is formed so as to form a step, the plug portion 32a enters the tip end opening 29a of the male luer part 25 to liquid tightly occlude the tip end opening 29a. Also, the diameter of the rear side portion of the plug portion 32a in the occluding portion 32 is larger than that of the tip end opening 29a, whereby the plug portion 32a can not be entered into the tip end opening 29a. The oscillation preventing portion 33 is slidable in the axial direction relative to the inner peripheral surface of the male luer rear portion 26 and not rotatable about the axis, thereby preventing the occluding portion 32 from oscillating and rotating as the male luer occluding portion 30 is moved in the front to back.

Further, the rear side portion of the occluding portion 32 is formed to have a smaller diameter than that at the front side portion thereof, and this narrow diameter portion is penetrated into the stretch hole 21 of the elastic seal portion 20.

Figure 9:
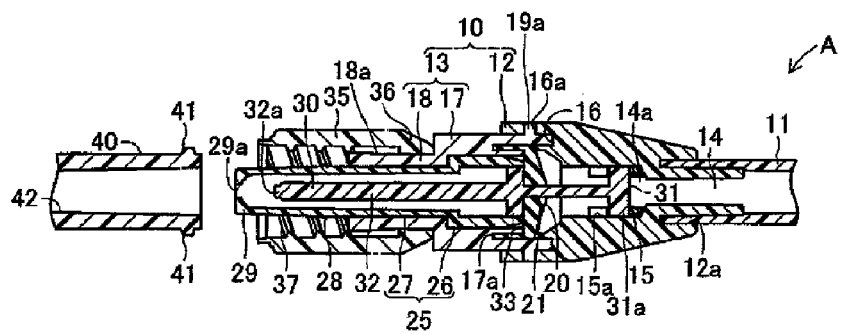
FIG. 9 is a cross sectional view illustrating the condition in which the male luer connector is detached from the female luer connector.

Also, the outer peripheral surface of the narrow diameter portion of the occluding portion 32 can be tightly contacted with the inner peripheral surface of the stretch hole of the elastic seal portion 20 and, as shown in FIGS. 3 and 9, between the outer peripheral surface of the occluding portion 32 and the stretch hole 21 of the elastic seal portion 20 is liquid tightly occluded when the elastic seal portion 20 is not pushed toward the rear side by the male luer part 25.

This male luer occluding portion 30 is configured such that it is activated toward the front side in response to the returned width as the stretch hole 21 of the elastic seal portion 20 is returned to the original state from the opened state. Therefore, the pressure force is not applied to the male luer part 25 to move from the front to the back, as shown in FIGS. 3 and 4, when the male luer part 25 is positioned at the front side by the activating force of the elastic seal portion 20, the male luer occluding portion 30 is also positioned and maintained at the front side by the elastic seal portion 20. At that time, the plug portion 32a enters the tip end opening 29a of the male luer part 25 to liquid tightly occlude the tip end opening 29a and between the outer peripheral surface of the occluding portion 32 and the stretch hole 21 of the elastic seal portion 20 is liquid tightly occluded. Also, the rear portion of the drive portion 31 is positioned at the rear end side of the play surface 15a of the basal end connecting portion 12.

Figure 6:
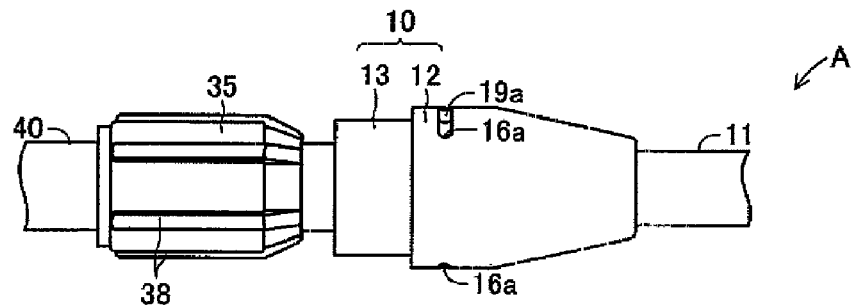
FIG. 6 is a side view illustrating the male luer connector and the female luer connector of FIG. 5.
Figure 8:
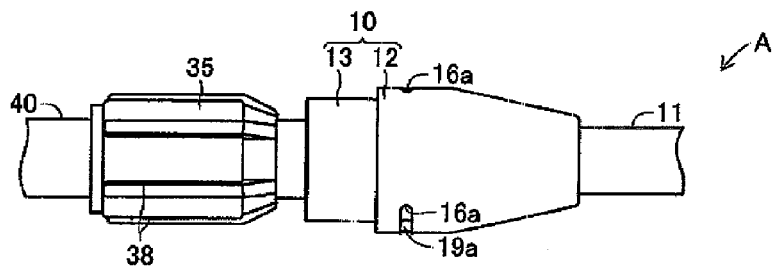
FIG. 8 is a side view illustrating the male luer connector and the female luer connector of FIG. 7.

In that condition, when the male luer part 25 is pushed rearwardly against the elastic force of the elastic seal portion 20, as shown in FIGS. 5 and 6, the male luer part 25 together with the male luer occluding portion 30 is rearwardly moved. According to this, the stretch hole 21 of the elastic seal portion 20 is opened and the rear end portion of the drive portion 31 is contacted with the front end portion of the internal thread portion 15 of the basal end connecting portion 12. And, by the basal end connecting portion 12 is rotated in the axial direction relative to the tip end supporting portion 13, the external thread portion 31a of the drive 31 is helically engaged with the internal thread portion 15 thereof to move the male luer occluding portion 30 rearwardly. Accordingly, as shown in FIGS. 7 and 8, the plug portion 32a is moved rearwardly from the tip end opening 29a of the male luer part 25 to open the tip end opening 29a.

A lock ring 35 is formed into a generally cylinder shape in which the inner peripheral surface of the basal end portion 36 is narrower in the diameter than those at the other portions of the inner peripheral surface. Also, the basal end portion 36 of the lock ring 35 is slidably engaged with the recess 18a of the supporting portion 18. Therefore, the lock ring 35 is rotatable about the axis relative to the supporting portion 18 and the moveable in the axial direction of the supporting portion 18. Further, an engagement thread portion 37 is formed from the tip end portion in the inner peripheral surface of the lock ring 35 to the center side portion in the axial direction. Then, to the outer peripheral surface of the lock ring 35, a projecting streak 38 as a slip stopper extended in the axial direction with a constant distance in the circumferential direction.

The male luer connector A configured in this way, as shown in FIGS. 3 to 10, is attached and detached to the female luer connector 40. The female luer connector 40 is formed into a cylinder in which a tube (not shown) as another tube member of the invention is connected to the rear end portion. Also, to the front end portion in the outer peripheral surface, thread portions to be engaged 41 formed by a pair of projections that can be helically engaged with the engagement thread portion 37 of the lock ring 35 is provided in the circumferential direction with a distance. Moreover, the inner peripheral surface 42 of the female luer connector 40 is formed into a gradual taper in which the diameter at the opening side is large and it is decreased as closed to the deeper side, whereby the male luer front portion 27 of the male luer connector A is liquid tightly coupled with this inner peripheral surface 42.

Further, the tip end side portion of the female luer connector 40 is formed having a dimension such that it can be received between the inner peripheral surface of the lock ring 35 and the male luer front portion 27 and coupled to the male luer connector A by helically engaging the engagement portion 37 with the thread portion to be engaged 41 while including the male luer front portion 27 therein. According to this, between the tube 11 and the tube connected to the rear portion of the female luer connector 40 can be communicated with each other through the male luer connector A and the female luer connector 40.

When the male luer connector A configured in this way is coupled to the female luer connector 40, firstly, a priming is carried out to fill the medicinal liquid within the flow path 14 of the male luer connector A and, then, as shown in FIGS. 3 and 4, the tip end portion of the male luer connector A and the tip end opening, opposed to each other, are approached to each other. Next, the male luer front portion 28 of the male luer part 25 is inserted the inside of the female luer connector 40. As a result, the outer peripheral surface of the male luer front portion 27 is liquid tightly contacted with the inner peripheral surface 42 of the female luer connector 40 and the male luer part 25 together with the male luer occluding portion 30 is moved within the male luer connector body 10 by the pushing pressure thereby to provide the condition as shown in FIGS. 5 and 6.

In this case, with the projection 28 of the male luer part 25 is contacted with the tip end portion of the supporting portion 18, the rearward movement of the male luer part 25 with the male luer occluding portion 30 is stopped. Then, the tip end opening 29a of the male luer part 25 is maintained occluded by the plug portion 32a of the male luer occluding portion 30 and the stretch hole 21 of the elastic seal portion 20 is opened by the pushing pressure of the male luer part 25. According to this, the tube 11, the flow path 14 and the inside of the male luer part 25 are communicated. Then, once the engagement thread portion 37 of the lock ring 35 is contacted with the thread portion to be engaged 41, the engagement thread portion 37 is helically engaged with the thread portion to be engaged 41 by rotating the lock ring 35 in the predetermined axial direction. And, the lock ring 35 is rotated until the proper condition of the helical engagement of the engagement thread portion 37 with the thread portion to be engaged 41 is obtained.

At that time, the rear end portion of the drive portion 31 of the male luer occluding portion 30 is contacted with the front end portion of the internal thread portion 15 of the basal end connecting portion 12. Therefore, by rotating the basal end connecting portion 12 about the axis relative to the tip end supporting portion 13, the external thread portion 31a of the drive portion 31 is helically engaged with the internal thread portion 14 provided to the basal end connecting portion 12 to reawardly move the male luer occluding portion 30. Further, when the male luer occluding portion 30 is rearwardly moved, the male luer occluding portion 30 is contacted with the inner peripheral surface of the male luer rear portion 26 to control the rotation about the axis and smoothly moved rearwardly. According to this, as shown in FIGS. 7 and 8, the plug portion 32a is backwardly moved from the tip end opening 29a of the male luer part 25 to open the tip end opening 29a. At that time, the male luer occluding portion 30 can smoothly moved without oscillating by the oscillation preventing portion 33 is slidably moved relative to the inner peripheral surface of the male luer rear portion 26.

Moreover, when a liquid transfusion line set in which the tube 11 is communicated with the tube connected to the female luer connector 40 is used to a patient, the downstream end of the tube connected to the female luer connector 40 is punctured to the body of the patient to connect the puncturing member such as an indwelling needle and the like (not shown) to be indwelled therein. Then, a medicinal liquid is flowed from an infusion cylinder into the tube 11 and the air in the female luer connector 40 or the tube is discharged to the exterior, and the puncturing member is punctured to the predetermined site in the body of the patient to supply a set certain flow of the medicinal liquid into the body of the patient by adjusting.

Figure 10:
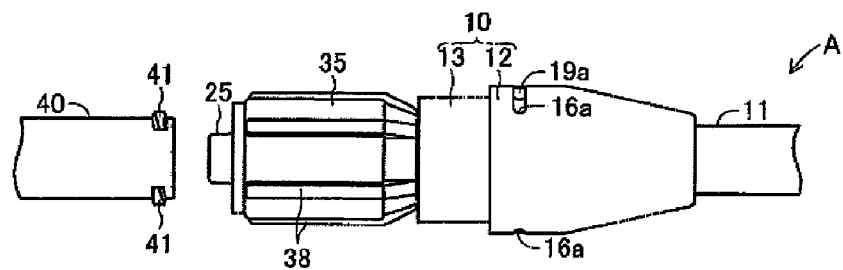
FIG. 10 is a side view illustrating the male luer connector and the female luer connector of FIG. 9.
Figure 11:
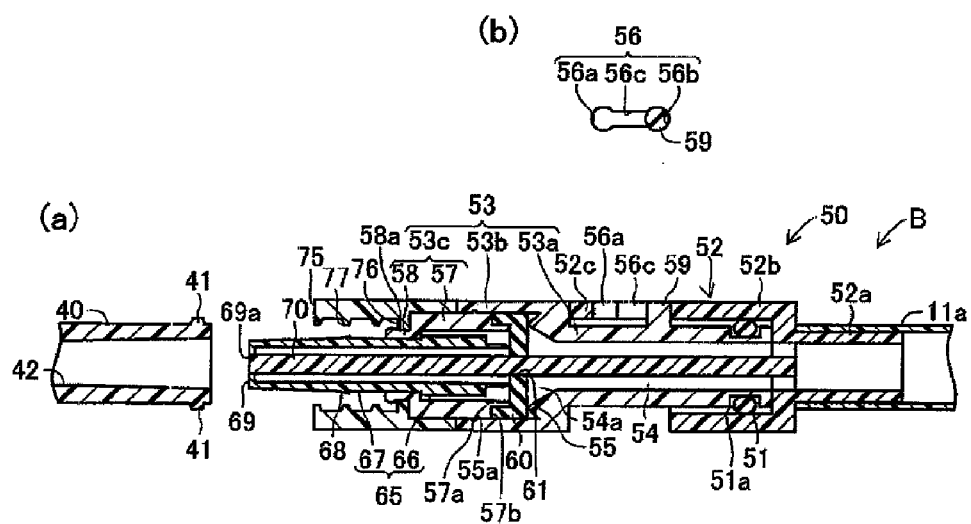
FIG. 11 shows the male luer connector in accordance with the second embodiment prior to be connected to the female luer connector.
Figure 12:
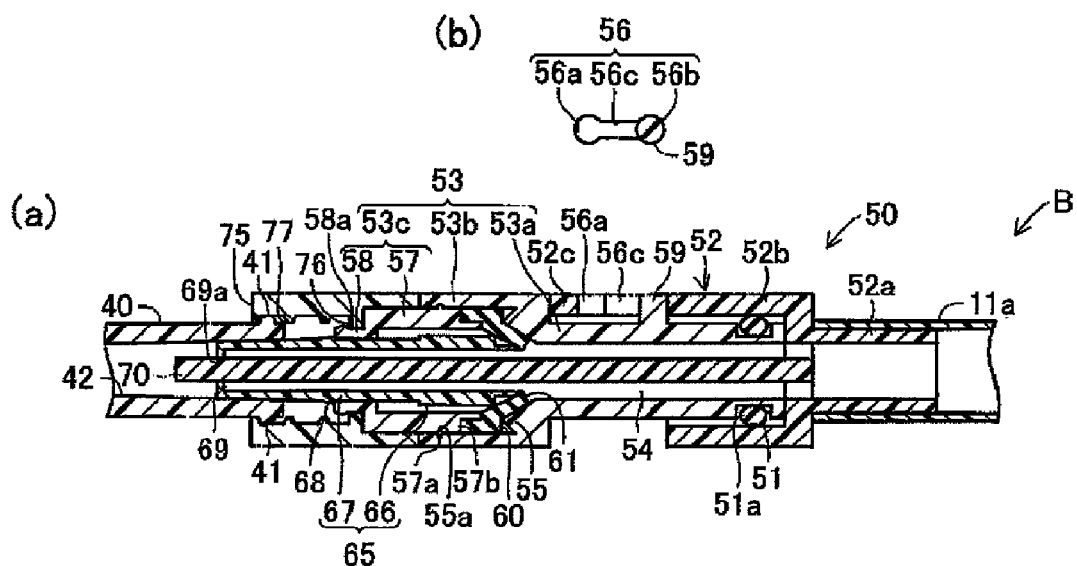
FIG. 12 shows the male luer connector in accordance with the second embodiment that is being connected to the female luer connector.
Figure 13:
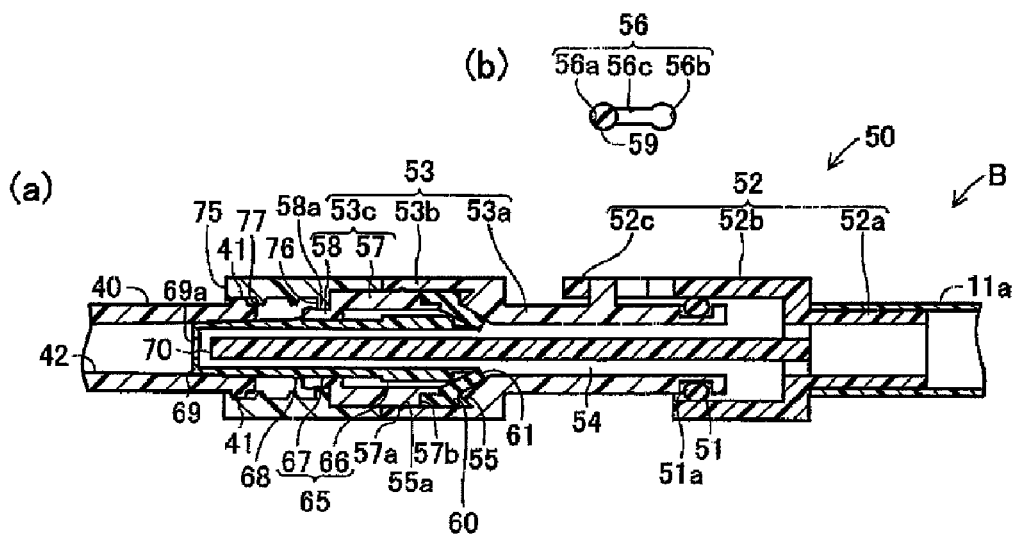
FIG. 13 shows the male luer connector in accordance with the second embodiment connected to the female luer connector.

Further, when the use of the liquid transfusion line set is completed and the male luer connector A is decoupled from the female luer connector 40, the lock ring 35 is rotated in the direction opposed to the predetermined direction as described in above. And, when the female luer connector 40 is decoupled from the male luer connector A, the activating force to rearwardly move the male luer part 25 is released and the male luer part 25 is forwardly moved by the restoration force of the elastic seal portion 20 to become in the condition as shown in FIGS. 9 and 10. In that condition, between the outer peripheral surface of the occluding portion 32 and the stretch hole 21 of the elastic seal portion 20 is liquid tightly occluded, thereby eliminating the leakage of the medical liquid from the tip end opening 29a of the male luer part 25.

Further, prior to release the lock ring 35, the basal end connecting portion 12 is rotated in the direction opposed to the above described direction relative to the tip end supporting portion 13, whereby the male luer occluding portion 30 can be forwardly moved. According to this, since the helical engagement between the internal thread 15 and the external thread 31 is released and the male luer occluding portion 30 becomes moveable in the axial direction, the male luer part 25 in which the tip end opening 29a is occluded by the plug portion 32, together with the male luer occluding portion 30 is forwardly moved by the restoration force of the elastic seal portion 20 to provide the same condition as shown in FIGS. 3 and 4.

As described in above, in the male luer connector A in accordance with the embodiment of the invention, by rotating the basal end connecting portion 12 in one direction relative to the tip end supporting portion 13, the tip end opening 29a of the male luer part 25 can liquid tightly be occluded by the plug portion 32a of the male luer occluding portion 30. In this way, since the tip end opening 29a of the male luer part 25 can liquid tightly occluded, the generation of bacteria at the tip end opening 29a of the male luer part 25 can be prevented while the male luer connector A is not used. And, at the priming is carried out, since the medicinal liquid in the male luer connector A can be prevented from being spilled out of the tip end opening 29a of the male luer part 25, it can be prevented that the medicinal liquid is spilled out and attached to the outer surface of the male luer connector A and bacteria is generated at the attached portion. As well as, the waste of the medical liquid by spilling out can be reduced.

Moreover, from the condition where the tip end opening 29a of the male luer part 25 is liquid tightly occluded by the male luer occluding portion 30, the basal end connecting portion 12 is rotated in the other direction relative to the tip end supporting portion 13, whereby the tip end opening 29a of the male luer part 25 is opened as the male luer occluding portion 30 is apart from the tip end opening 29a of the male luer part 25. Therefore, when the male luer connector A is coupled to the female luer connector 40, the liquid can be flowed through from the male luer connector A to the female luer connector 40 by opening the tip end opening 29a of the male luer part 25 as described in above.

Moreover, according to the embodiment of the invention, within the guide holes 16a and 16a of the basal end connecting portion 12, the guide projections 19a and 19a of the sliding portion 17 are located and since these guide projections 19a and 19a can be seen from the exterior, it can be easily checked that whether the tip end opening 29a of the male luer part 25 is in the opening or closing. According to this, the error operation of the male luer connector A can be prevented. Further, within the male luer connector body 10, the elastic seal portion 20 having the stretch hole 21 is provided, therefore, when the male luer part 25 is located at the front side, the flow path 14 in the male luer connector body 10 can be occluded.

Second Embodiment

FIGS. 11 to 14 show a male luer connector B of the second embodiment in accordance with the invention and the female luer connector B to be coupled to the male luer connector B. The male luer connector B comprises a male luer connector body 50 formed into a generally cylindrical shape; an elastic seal portion 60 provided in the inside of the male luer connector body 50 at the portion slightly more front side than the about the center, a male luer part 65 provided in the inside of the male luer connector body 50 from the front side of the elastic seal portion 60 to the tip end side outside of the male luer connector body 50, a male luer occluding portion 70 provided in the male luer connector body 50 and the male luer part 65, and a lock ring 75 attached to the tip end side outer periphery of the male luer connector body 50.

The male luer connector body 50 comprises a stepped cylindrical basal end connecting portion 52, and a stepped cylindrical tip end supporting portion 53 extended from the tip end side to the front side of the basal end connecting portion 52, in which the inside of the body 50 is formed into a flow path 54 for flowing a medicinal liquid. Also, a space 54a having a diameter that is increased from the rear end side to the fore side is formed to the tip end portion of the flow path 54. The basal end connecting portion 52 comprises a basal end portion 52a connected to the tube 11a, a large diameter portion 52b at the tip end side, and a guide hole forming portion 52c having an arc like cross section and forwardly extending from one portion of the tip end surface of the large diameter portion 52b.

Then, over the boundary portion between the guide hold forming portion 52c and the large diameter portion 52b in the center portion in the width direction of the guide hole forming portion 52c through the fore side of the guide hole forming portion 52c, a guide hole 56 penetrating between the outer surface and the inner surface of the guide hole forming portion 52c is formed. In this guide hole 56, as shown in plane views in FIGS. 11(b), 12(b), 13(b) and 14(b), the tip end portion is formed to a generally circular tip end static portion 56a opened at the rear portion, and the front portion thereof is formed into a generally circular rear end static portion 56b. Also, the tip end static portion 56a is communicated with the rear end static portion 56b by a pathway 56c having a width shorter than the diameters of the tip end static portion 56a and the rear end static portion 56b and extending in the front to back direction.

The tip end supporting portion 53 is formed into a stepped cylinder connected to the basal end connecting portion 52 so as to be moveable in the axial direction and comprises a small diameter sliding portion 53a disposed so as to be moveable in the axial direction within the large diameter portion 52b of the basal end connecting portion 52, a large diameter connecting portion 53b extended from the tip end to the front side of the sliding portion 53a, and a supporting portion 53c made by a different member attached to the tip end side inner periphery of the connecting portion 53b and forwardly extended from the connecting portion 53b. To the rear side of the outer peripheral surface of the sliding portion 53a, a seal attachment recess 51 is formed along the circumference thereof. Also, into the seal attachment recess 51, an O ring 51a is attached. In this O ring 51a, one portion of the outer periphery is projected from the seal attachment recess 51 to contact with the inner peripheral surface of the large diameter portion 52b, whereby between the outer peripheral surface of the sliding portion 53a and the inner peripheral surface of the large diameter portion 52b is liquid tightly sealed.

Moreover, at about the center in the outer peripheral surface of the sliding portion 53a, a cylindrical guide projection 59 that can be engaged with the tip end static portion 56a and the rear end static portion 56b and passed through the pathway 56c is formed. Although the diameter of the guide projection 59 is slightly larger than the width of the pathway 56c, the guide projection 59 moves within the pathway 56c as if it expands the pathway 56 in the width direction by applying the force to move the tip end supporting portion 53 relative to the basal end connecting portion 52 in the front to back direction. And, when the guide projection 59 is located in the inside of the tip end static portion 56a or the rear end static portion 56b, the guide projection 59 (the tip end supporting portion 53) is maintained static at the location as the force to move the tip end supporting portion 53 relative to the basal end connecting portion 52 is released.

In this way, in the sliding portion 53a, the O ring 51a is mounted in the seal attachment recess 51 and the guide projection 59 is disposed within the guide hole 56, in that condition, the rear end side portion is disposed within the large diameter portion 52b, whereby the sliding portion 53a can be moved in the axial direction by the distance between the tip end static portion 56a and the rear end static portion 56b. Further, a step portion is formed between the front end portion of the sliding portion 53a and the rear end portion of the connecting portion 53b, in which the rear surface of the connecting portion 53b formed by this step portion is contacted with the front end portion of the guide hole forming portion 52c when the tip end supporting portion 53 is located at the last portion within the moveable range thereof as shown in FIG. 11(a).

Also, at the portion corresponding to the step portion as described in above in the inside of the connecting portion 53b, a ring like projection 55 having a generally triangular cross section and forwardly projecting is formed along the circumference, in which a space 54a is formed by the inner peripheral surface of this ring like projection 55. Then, in order to the supporting portion 53c is attached to the fore side in the inner peripheral surface of the connecting portion 53b, an engagement groove 55a is formed along the circumference thereof. Also, the supporting portion 53c is formed into a stepped cylinder and comprises a connected portion 57 connected to the connecting portion 53b and a tip end portion 58 forwardly extended from the front end center side of the connected portion 57.

Further, at the rear side portion of the outer peripheral surface of the connected portion 57, an engagement projection 57a to be engaged with the engagement groove 55a of the connecting portion 53b is formed, in which by this engagement projection 57a is engaged with the engagement groove 55a, the supporting portion 53c is coupled to the connecting portion 53b. Also, to the rear end outer periphery of the connected portion 57, a step portion 57b having a diameter smaller than that at the front side portion of the connected portion 57 is formed, in which the elastic seal portion 60 is fixed by inserting the peripheral edge thereof into the gap formed by this step portion 57b and the inner peripheral surface of the connecting portion 53b.

The rear surface outer peripheral portion of the elastic seal portion 60 is contacted with the ring like projection 55 of the connecting portion 53b, whereby the elastic seal portion 60 is prevented from being out of the gap formed by the step portion 57b and the inner peripheral surface of the connecting portion 53b. Further, the elastic seal portion 60 is comprised by a generally disc like rubber having an elastic and stretch properties and provided with a stretch hole 61 for opening or closing by stretching at the center thereof. Accordingly, the elastic seal portion 60 is stretched by applying the predetermined pressure force to the fore surface thereof to open the stretch hole 61 while it is contracted by releasing the pressure force to close the stretch hole 61. When the stretch hole 61 is closed, the flow part 54 is occluded.

The tip end portion 58 is formed into a cylinder narrower than the connected portion 57 and step portions are formed between the inner peripheral surface of the supporting portion 53 and the rear end portion of the tip end portion 58 in the outer peripheral surface thereof and the front end portion of the connected portion 57, respectively. Moreover, to the portion except for the tip end portion in the outer peripheral surface of the tip end portion 58, a recess 58a for sliding having an outer diameter slightly smaller than that at the tip end portion is formed. Also, within the supporting portion 53c, the cylindrical male luer part 65 is attached so as to be slidable in the axial direction. This male luer part 65 is formed into a two stepped cylinder in which the rear side has a larger diameter while the tip end side has a narrower diameter, in which a male luer rear portion 66 at the rear side is moveable in the axial direction within the inside of the supporting portion 53c. Also, to the rear end portion of the outer peripheral surface of the male luer rear portion 66, a step portion having a smaller diameter is formed and the rear end of the male luer rear portion 66 is widely opened rearwardly.

The portion from the fore side to the center side of the male luer rear portion 66 is formed into a cylinder having a certain outer diameter with a certain maintained distance from the inner peripheral surface of connected portion 57. Further, the diameter at the fore side portion of the male luer rear portion 66 is greater than the diameter of the inner peripheral surface of the tip end portion 58, whereby the front end surface of the male luer rear portion 66 is contacted with between the rear end portion of the tip end portion 58 and the front end portion of the connected portion 58 as the male luer part 65 is forwardly moved within the supporting portion 53c not to forwardly move the male luer part 65 further.

The male luer front portion 67 forming the tip end portion of the male luer part 65 is formed into a cylinder having a gradual taper in which the diameter thereof is decreased from the rear side portion to the tip end side. Further, to the portion slightly more fore side than the center in the front to back direction in the outer peripheral surface of the male luer front portion 67, a small projection 68 is formed along the circumference thereof. Therefore, when the male luer part 65 is rearwardly moved within the supporting portion 53c, as shown in FIGS. 12(a) and 13(a), the projection 68 is contacted with the tip end portion of the tip end portion 58, whereby the male luer part 65 can not be moved further to the rear side the supporting portion 53c. Also, in that condition, the elastic seal portion 60 is rearwardly pushed by the male luer part 65 to open the stretch hole 61. Further, to the tip end portion of the male luer front portion 67, a small diameter end surface 69 and, in turn, a small diameter tip end opening 69a is formed at the center portion thereof.

The male luer occluding portion 70 is extended from the boundary between the basal end portion 52a and the large diameter 52b in the inside of the basal end connecting portion 52 and the inside of the male luer connector body 50 and the male luer part 65 forwardly, and the outer peripheral surface of the rear end portion is secured to the inner peripheral surface of the boundary portion between the basal end portion 52a and the large diameter portion 52b by a plurality of connectors (not shown). The male luer occluding portion 70 is formed into a stick body having the even diameter from the rear end to the front end and a circular cross section, and the front end side portion enters the tip end opening 69a of the male luer part 65 to liquid tightly occlude the tip end opening 69a. Further, the male luer occluding portion 70 penetrates the stretch hole 1 of the elastic seal portion 60 and tightly contacts with the inner peripheral surface of the stretch hole 61 to occlude the flow path 54.

The lock ring 75 is formed into a generally cylindrical shape, in which the inner peripheral surface of the basal end portion has a larger diameter than that at the other portion. Also, to the front end of the larger diameter portion in the inner peripheral surface of the lock ring 75, a projection 76 to be engaged with the recess 58a of the tip end portion 58 so as to be rotatable about the axis. This lock ring 75 receives the connected portion 57 within the rear end side thereof and is mounted to the supporting portion 53c with the projection 75 engaged with the recess 58a. Accordingly, the lock ring 75 is rotatable relative to the supporting portion 53c in the axial direction. Also, an engagement thread portion 77 is formed from the tip end portion to the portion of the projection 76 in the inner peripheral surface of the lock ring 75. Since the female luer connector 40 to which the male luer connector B in accordance with the embodiment of the invention is connected is the same as the female luer connector 40 of the embodiment as described in above, the like components are indicated by the like numerical numbers.

When the male luer connector B configured in this way is coupled to the female luer connector 40, after the aforementioned priming is carried out, as shown in FIG. 11(a), the tip end portion of the male luer connector B is opposed and approached to the tip end opening of the female luer connector 40. Next, the male luer front portion 67 of the male luer part 65 is inserted into the inside of the female luer connector 40. According to this, the outer peripheral surface of the male luer front portion 67 is liquid tightly contacted with the inner peripheral surface of the female luer connector 40, then, the male luer part 65 allows the male luer connector body 50 to move rearwardly by the pushing pressure thereof.

In this case, the rearward movement of the male luer part 65 is stopped as the projection 68 of the male luer part 65 is contacted with the tip end surface of the tip end portion 58. Then, in the tip end side portion of the male luer occluding portion 70, the tip end opening 69a is maintained to be occluded while the tip end side portion is forwardly projected from the tip end opening 69a of the male luer part 65, and the stretch hole 61 of the elastic seal portion 60 is opened by the pushing pressure of the male luer part 65. According to this, the tube 11a, the flow path 54 and the inside of the male luer part 65 are communicated with one another. Then, by rotating the lock ring 75 in the predetermined axial direction, the engagement thread portion 77 is helically engaged with the thread portion to be engaged 41. And, the lock ring 75 is rotated to provide the proper helical engagement of the engagement thread portion 77 with the thread portion to be engaged, or the condition as shown in FIG. 12(a).

Next, by rearwardly moving the basal end connecting portion 52 relative to the tip end supporting portion 53, as shown in FIG. 13(a), the tip end portion of the male luer occluding portion 70 is backwardly moved from the tip end opening 69a of the male luer part 65 to open the tip end opening 69a. At that time, as shown in FIGS. 12(b) and 13(b), the guide projection 59 is moved from within the rear end static portion 56b of the guide hole 56 to within the tip end static portion 56a. According to this, it can be checked that the tip end opening 69a is opened. And, as described in above, the medicinal liquid is supplied into the body of the patient by the set certain flow rate by adjusting with the use of the liquid transfusion line.

Further, when the male luer connector B is detached from the female luer connector 40 after the completion of the use of the liquid transfusion line set, the lock ring 75 is rotated in the direction opposed to the predetermined direction as described in above to detach the female luer connector 40 from the male luer connector B. According to this, the activating force to move the male luer part 65 rearwardly is released and the male luer part 65 is forwardly moved by the restoration force of the elastic seal portion 60 to provide the condition as shown in FIG. 14(a). In that condition, since between the outer peripheral surface of the male luer occluding portion 70 and the stretch hole 61 of the elastic seal portion 60 is liquid tightly occluded, the medicinal liquid is not leaked from the tip end opening 69a of the male luer part 65.

Also, in this case, prior to the release of the lock ring 75 is applied, the basal end connection portion 52 is forwardly moved relative to the tip end supporting portion 53, thereby occluding the tip end opening 69a of the male luer part 65 by the tip end portion of the male luer occluding portion 70. According to this, when the female luer connector 40 is detached from the male luer connector B, as in FIG. 11, the tip end opening 69a and the stretch hole 61 both are in the opened status.

As described in above, in the male luer connector B in accordance with the embodiment of the invention, the basal end connecting portion 52 is forwardly moved relative to the tip end supporting portion 53, whereby the tip end opening 69a of the male luer part 65 can be liquid tightly occluded at the tip end portion of the male luer occluding portion 70. Further, the basal end connecting portion 52 is rearwardly moved relative to the tip end supporting portion 53 from the condition in which the tip end opening 69a of the male luer part 65 is liquid tightly occluded by the male luer occluding portion 70, whereby the tip end opening 69a of the male luer part 65 can be opened by backwardly moving the tip end portion of the male luer occluding portion 70 from the tip end opening 69a of the male luer part 65. Therefore, the medicinal liquid can be flowed from the male luer connector B side to the female luer connector 40 side.

Moreover, in accordance with this embodiment, when the basal end connecting portion 52 is not operated to move relative to the tip end supporting portion 53, since the guide projection 59 is maintained static within the rear end static portion 56b and the tip end static portion 56a of the guide hole, it can be prevented that the tip end opening 69a of the male luer part 65 is suddenly opened or closed. Also, it can be easily checked that whether the tip end opening 69a of the male luer part 65 is opened or closed by the location of the guide projection 59 within the guide hole 56. The other effects of this embodiment of the invention are the same those obtained by the first embodiment.

Figures 14, 15, 16:
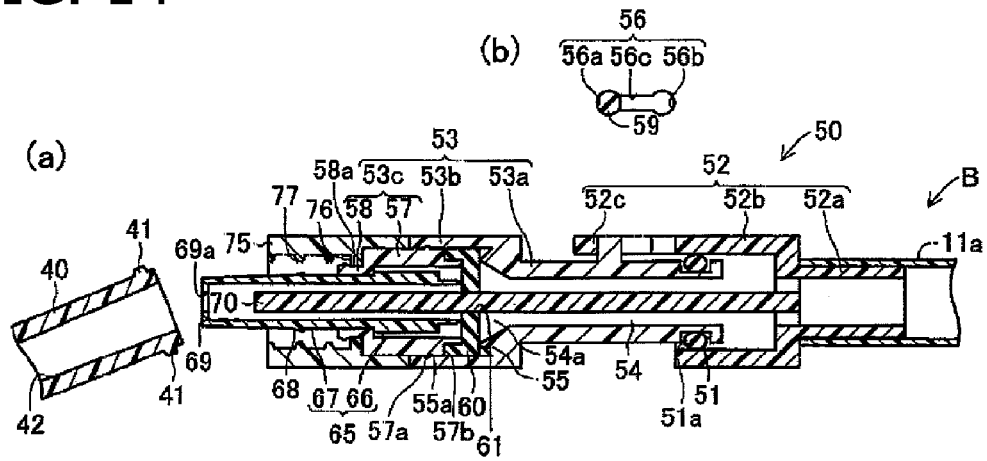
FIG. 14 shows the female luer connector detached from the male luer connector in accordance with the second embodiment.
FIG. 15 is a cross sectional view illustrating the male luer connector in accordance with the third embodiment of the invention prior to be connected to the female luer connector.
FIG. 16 is a cross sectional view illustrating the condition in which the male luer connector in accordance with the third embodiment of the invention is connected to the female luer connector.

FIGS. 15 and 16 show a male luer connector C in accordance with a third embodiment of the invention as well as the female luer connector 40 to be coupled to the male luer connector C. The male luer connector C comprises a male luer connector body 80 formed into a generally cylindrical shape, an elastic seal portion 90 provided at the portion slightly more front side than the general center in the inside of the male luer connector body 80, a male luer part 95 provide d from the front side of the elastic seal portion 90 in the inside of the male luer connector body 80 to the front side outer portion of the male luer connector body 80, a male luer occluding portion 70c provided in the inside of the male luer connector body 80 and the male luer part 95, and a lock ring 75 attached to the tip end side outer periphery of the male luer connector body 80.

The male luer connector body 80 comprises a generally cylindrical basal end connector portion 82, and a stepped cylindrical tip end supporting portion 83 covering from the general center to the front end side of the basal end connecting portion 82 and forwardly extending further, in which a flow path 84 through which the medicinal liquid is flowed. Also, to the tip end side portion of the flow path 84, a space 84a having a diameter increased from the rear end side to the fore end side is formed. To the generally central portion in the axial direction in the outer peripheral surface of the basal end connecting portion 82, a pair of ring like wall portions is formed by apart from each other, in which a seal attachment recess 81 is formed between the pair of wall portions and the outer peripheral surface of the basal end connecting portion 82. And, an O ring 81a is mounted within the seal attachment recess 81. Further, a tube 11 is connected to the rear end portion of the seal attachment recess 81 in the outer peripheral surface of the basal end connecting portion 82 and an external thread portion 85 is formed to the fore side portion of the seal attachment recess 82 in the outer peripheral surface of the basal end connecting portion 82.

The tip end supporting portion 83 is formed by a stepped cylinder coupled to the basal end connecting portion 82 so as to be rotatable in the axial direction, and comprises a sliding portion 83a attached to the basal end connecting portion 82 in the condition in which an internal thread portion 85a formed on the inner peripheral surface is helically engaged with the external thread portion 85 of the basal end connecting portion 82 to be rotatable in the axial direction, grasping portion 83b rearwardly extended from the rear end side of the sliding portion 83a, and a supporting portion 83c attached to the tip end side inner periphery of the sliding portion 83a and forwardly extended from the sliding portion 83a. These sliding portion 83a, the grasping portion 83b and the supporting portion 83c are made from different members and assembled to each other to provide the tip end supporting portion 83.

Then, a narrow diameter portion 86 having an outer diameter smaller than that of the other portion is formed to the rear side in the outer peripheral surface of the sliding portion 83a, in which the grasping portion 83b allows this narrow diameter portion 86 to insert into the tip end side inside to coupled to the sliding portion 83a. Further, the outer peripheral surface of the O ring 81a provided within the seal attachment recess 81 is pressurized to contact with the inner peripheral surface of the grasping portion 83b, whereby between the sliding portion 83a and the grasping portion 83b can be liquid tightly sealed. Also, the outer peripheral surface of the rear end portion of the male luer occluding portion 70c is secured to the front side portion in the inner peripheral surface of the basal end connecting portion 82 by a plurality of connecting pieces (not shown). The other components of the male luer connector C and the female luer connector 40 are the same as those of the male luer connector C and the female luer connector 40 described in the second embodiment. Therefore, the explanation thereof is omitted by indicating the same numerical numbers to the same components.

When the male luer connector C configured in this way is coupled to the female luer connector 40, as shown in FIG. 15, the tip end portion of the male luer connector C is opposed to the tip end opening of the female luer connector 40 to close to each other after the priming described in above. Then, the male luer front portion 67 of the male luer part 95 is inserted into the inside of the female luer connector 40. According to this, the outer peripheral surface of the male luer front portion 67 is liquid tightly contacted with the inner peripheral surface 42 of the female connector 40 and, then, the male luer part 95 is rearwardly moved within the male luer connector body 80 by the pushing pressure.

In this case, the rearward movement of the male luer part 95 is stopped as the projection 68 of the male luer part 95 is contacted with the tip end surface of the tip end portion 58. Then, the engagement thread portion 77 is helically engaged with the tread portion to be engaged 41 by rotating the lock ring 75c in the predetermined axial direction to provide the proper helical engagement of the engagement thread portion 77 and the thread portion to be engaged 41. In that condition, the internal thread portion 85a is helically engaged with the external thread portion 85 of the basal end connecting portion 82 by rotating the tip end supporting portion 83 relative to the basal end connecting portion 82 by grasping the grasping portion 83b to backwardly move the male luer occluding portion 70c from the tip end opening 69a of the male luer part 95. As a result, as shown in FIG. 16, both the tip end opening 69a of the male luer part 95 and the stretch hole 61 of the elastic seal portion 90 are opened.

Then, the medicinal liquid is supplied into the body of the patient by the set certain flow rate by adjusting with the use of the liquid transfusion line. Also, in this case, when the female luer connector 40 is detached from the male luer connector B after the completion of the use of the liquid transfusion set, the activating force to move the male luer part 65 rearwardly is released and the male luer part 95 is forwardly moved by the restoration force of the elastic seal portion 90. Since between the outer peripheral surface of the male luer occluding portion 70c and the stretch hole 61 of the elastic seal portion 90 is liquid tightly occluded, the medicinal liquid is not leaked from the tip end opening 69a of the male luer part 95.

As described in above, in the male luer connector C in accordance with the embodiment of the invention, the basal end connecting portion 82 is forwardly moved relative to the tip end supporting portion 83, whereby the tip end opening 69a of the male luer part 95 can be liquid tightly occluded at the tip end portion of the male luer occluding portion 70c. Further, the basal end connecting portion 82 is rearwardly moved relative to the tip end supporting portion 83 from the condition in which the tip end opening 69a of the male luer part 95 is liquid tightly occluded by the male luer occluding portion 70c, whereby the tip end opening 69a of the male luer part 95 can be opened by backwardly moving the tip end portion of the male luer occluding portion 70c from the tip end opening 69a of the male luer part 95. Therefore, the medicinal liquid can be flowed from the male luer connector C side to the female luer connector 40 side. Therefore, with this male luer connector C, the same effect obtainable by the male luer connector B can be provided.

The male luer connector in accordance with the invention is not intended to limited to the embodiments described in above, various modifications thereof may be made. For example, to the tip end opening 29a or the like of the male luer part 25 and the like, a filter that allows gas to flow but not liquid may be detachably provided. According to this, at the priming, it can be eliminated that the medicinal liquid in the flow path of the male luer connector A or the like is spilled out of the tip end opening 29a or the like of the male luer part 25 and the like. Further, in each embodiment described in above, though the male luer connector A and the like is assembled to a liquid transfusion set equipped with an infusion cylinder, the male luer connector A and the like may be used for connecting a blood transfusion lines or various tube members of another purpose other than the liquid transfusion line.

In the male luer connector in accordance with the invention of the embodiment as described above, by moving the male luer occluding part provided in the insides of the male luer connector body and the male luer part relative to the male luer part in the predetermined direction by operating the displacement mechanism, the tip end opening of the male luer part can be liquid tightly occluded at the tip end of the male luer occluding part. In this way, the tip end opening of the male luer part to be an outlet of a liquid can be liquid tightly occluded, thereby preventing bacteria from being generated at the tip end opening of the male luer part during unuse time of the male luer connector. Further, it can be achieved that a medicinal liquid in a flow path of the male luer connector is spilled out of the tip end opening of the male luer part to the exterior by configuring the male luer connector such that the tip end opening of the male luer part allows not a liquid but a gas passing there through at, for example, priming. As a result, it can be prevented that the medicinal liquid is spied out and attached to the outer surface of the male luer connector to cause the generation of bacteria around the attached portion. As well as, it can reduce to spill and waste the medicinal liquid.

Also, from the condition where the tip end opening of the male luer part is liquid tightly occluded by the male luer occluding part, the male luer occluding part is moved toward the opposed direction to the predetermined direction, as described in the above, relative to the male luer part, whereby the male luer occluding part can be apart from the tip end opening of the male luer part to open the tip end opening of the male luer part. Therefore, when the male luer connector is coupled with the female luer connector, the liquid can be flowed through from the male luer connector side to the female luer connector side by opening the tip end opening of the male luer part as described in above.

Moreover, since the movement of the male luer occluding part relative to the male luer part by operating the displacement mechanism is performed by using the displacement of the tip end supporting part relative to the basal end connecting part, the positional relationship between the male luer occluding part and the male luer part (whether the tip end opening of the male luer part is opened or closed) can easily checked. Accordingly, an error operation of the male luer connector may be reduced. The opening and closing the tip end opening of the male luer part in this case may be performed by moving the male luer occluding part relative to the male luer part positioned at the predetermined location within the tip end supporting part or may be performed by moving the male luer part together with the tip end supporting part relative to the male luer occluding part fixed to the basal end connecting part. Further, the male luer occluding part may be a stick like or cylindrical narrow long member having a tip end with which the tip end opening of the male luer part can be liquid tightly occluded.

The other configurational characteristic of the male luer connector in accordance with an embodiment of the invention is that, the male luer connector further comprises an elastic seal portion provided at near the boundary between the basal connecting part and the tip end supporting part within the male luer connector body, said elastic seal includes a stretchable hole being capable of occluding the flow path within the male luer connector body and being opened by pressing by the male luer part as moved toward the rear, thereby passing the male luer occluding part through said stretchable hole.

According to this, when the tip end of the male luer occluding part occludes the tip end opening of the male luer part by positioning both of the male luer part and the male luer occluding part, the inner peripheral surface of the stretchable hole of the elastic seal is tightly contacted to the male luer occluding part to also occlude the flow path within the male luer connector body. Furthermore, when the male luer occluding part is backwardly moved relative to the male luer part to open the tip end opening of the male luer part while the male luer part is backwardly moved to open the stretchable hole of the elastic seal, both of the stretchable hole of the male luer part and the tip end opening of the male luer part are opened. As a result, the supply of the liquid from the male luer connector to the female luer connector or the stop thereof can certainly be performed.

Moreover, yet another configurational characteristic of the male luer connector in accordance with an embodiment of the invention is that when the backwardly moving force of the male luer part is released, the male luer part is forwardly pushed back by the restoring force of the elastic seal to liquid tightly close between the peripheral surface of the stretchable hole and the male luer occluding part. According to this, when the pushing force against the male luer part to move toward rearward is not applied, the condition where the elastic seal occludes the rear end opening of the male luer part can be maintained.

Furthermore, another configirational characteristic of the male luer connector in accordance with an embodiment of the invention, the displacement mechanism allows to the basal end connecting part to rotate about the axis relative to the tip end supporting part and an inner threaded part is provided at the predetermined portion on the inner peripheral surface of the basal end connecting part as well as an outer threaded part capable of being helically engaged with the inner threaded part provided at the rear end side part of the male luer occluding part, whereby the male luer occluding part is movable relative to the basal end connecting part, in which the basal end connecting part is rotated about the axis relative to the top end supporting part while the inner threaded part is helically engaged with the outer threaded part to forwardly and backwardly move the tip end part of the male luer occluding part relative to the tip end part of the male luer part.

According to this, only with the simple operation of the rotation of the basal connecting part about the axis relative to the tip end supporting part, the tip end part of the male luer occluding part can be forwardly and backwardly moved relative to the tip end opening to the male luer part to open and close the tip end opening of the male luer part. In this case, it is preferred that, to the front side of the inner threaded part of the inner peripheral surface of the basal end connecting part, a play surface on which the rear end side portion of the male luer occluding part is movable in the axial direction is provided as well as the tip end part of the male luer occluding part can not be forwardly protruded from the tip end opening of the male luer part. According to this, when the male luer part is moved toward the rear, the male luer occluding part together with the male luer part is moved toward the rear while occluding the tip end opening of the male luer part to open the stretchable hole of the elastic seal. Also, by rotating the basal end connecting part, the tip end opening of the male luer part can be opened. Therefore, the stretchable hole of the elastic seal and the tip end opening of the male luer part can be phased to open.

Another configurational characteristic of the male luer connector in accordance with an embodiment of the invention is that the displacement mechanism is configured such that the tip end supporting part is movable in the axial direction relative to the basal connecting part as well as the rear end side part of the male luer occluding part is fixed to the predetermined portion of the basal end connecting part, whereby the tip end supporting part can be moved in the axial direction relative to the basal end connecting part to forwardly and backwardly move the tip end part of the male luer occluding part relative to the tip end opening of the male luer part.

According to this, only with the operation to move the tip end supporting part in the axial direction relative to the basal end connecting part, the tip end part of the male luer occluding part can be forwardly and backwardly moved relative to the tip end opening of the male luer part to open and close the tip end opening of the male luer part, thereby making easier the operation easier to open and close the tip end opening of the male luer part as well as simplifying the structure of the male luer connector.

Further, yet another configurational characteristic of the male luer connector in accordance with an embodiment of the invention is that the displacement mechanism is configured such that the basal end connecting part can be rotated about the axis relative to the tip end supporting part and an outer threaded part is provided on the outer peripheral surface of the basal end connecting part as well as an inner threaded part helically engageable with the outer threaded part of the basal end connecting part is provided on the inner peripheral surface of the tip end supporting part and the rear end side portion of the male luer occluding part is fixed to the predetermined portion of the basal end connecting part, whereby the tip end of the male luer occluding part can be forwardly and backwardly moved relative to the tip end opening of the male luer part by rotating the basal connecting part about the axis relative to the tip end supporting part.

According to this, with only the simple operation to rotate the basal end connecting part about the axis relative to the tip end supporting part, the tip end of the male luer occluding part can be forwardly and backwardly moved relative to the tip end opening of the male luer part to open and close the tip end opening of the male luer part. In this case, opening and closing of the stretchable hole of the elastic seal and the tip end opening of the male luer part are performed at the same time.

Moreover, further configurational characteristic of the male luer connector in accordance with an embodiment of the invention is that a threaded part to be engaged is provided on the outer peripheral surface of the female luer connector and a lock ring provided with an engagement threaded part capable of being engaged with the threaded part to be engaged on its inner peripheral surface is mounted to the outer peripheral surface of the tip end supporting part so as to be rotatable in the axial direction, in which the engagement threaded part is helically engaged with the threaded part to be engaged, thereby connecting the male luer connector with the female luer connector.

According to this, by engaging the engagement threaded part with the threaded part to be engaged once the male luer connector is inserted into the female luer connector, the male luer connector can securely be coupled with the female luer connector. In this case, it is preferred that the stretchable hole of the elastic seal can be opened by backwardly moving the male luer part when the inner peripheral surface of the female luer connector is liquid tightly contacted with the outer peripheral surface of the male luer part, in that condition, the displacement mechanism is operated to backwardly move the tip end of the male luer occluding part from the tip end opening of the male luer part to open the tip end opening, thereby communicating the male luer connector with the female luer connector.

What is claimed is:

1. A male luer connector for communicating one tube member with the other tube member by coupling with one tube member and a female luer connector to which the other tube member is connected, in which the male luer connector comprises:

a male luer connector body including a basal end connecting part coupled with the one tube member at the rear part thereof and a cylindrical tip end support part forwardly extended from the front part of the basal end connecting part and being capable of displacing relative to the basal end connecting part while the boundary between the basal end connecting part and the tip end support part is liquid tightly sealed;

a male luer part having a generally cylindrical shape and comprising a tip end side portion including an outer peripheral surface provided within the tip end support part so as to slidably moved within it in the axial direction in the condition where the tip end side portion is protruded from the tip end of the tip end support part and the outer peripheral surface of the tip end side portion is tapered from the rear side to the tip end side, whereby the male luer part is capable of being liquid tightly contacted with the tapered inner peripheral surface;

a male luer occluding part provided in the insides of the male luer connector and the male luer part which can liquid tightly occlude the tip end opening of the male luer part at the tip end thereof; and a displacement mechanism for forwardly and backwardly moving the tip end of the male luer occluding part relative to the tip end opening of the male luer part by moving the male luer occluding part relative to the male luer part in the axial direction by using the displacement of the tip end support relative to the basal end connecting part.

2. The male luer connector in accordance with claim 1, wherein said male luer connector further comprises an elastic seal portion provided at near the boundary between said basal connecting part and said tip end supporting part within said male luer connector body, said elastic seal includes a stretchable hole being capable of occluding the flow path within said male luer connector body and being opened by pressing by said male luer part as moved toward the rear, thereby passing said male luer occluding part through said stretchable hole.

3. The male luer connector in accordance with claim 1, wherein when the force to rearwardly move said male luer part is released, said male luer part is returned to the front side by the restoration force of the said elastic seal portion, whereby between the periphery of the stretch hole of the said elastic seal portion and said male luer occluding portion is liquid tightly sealed.

4. The male luer connector in accordance with claim 1, wherein said displacement mechanism is configured such that said basal end connecting portion is rotatable in the axial direction relative to said tip end supporting portion, an internal thread portion is provided to the predetermined portion of the inner peripheral surface of said basal end connecting portion and an external thread portion that can be helically engaged with said internal thread portion is provided at the rear end side portion of said male luer occluding portion whereby said male luer occluding portion becomes moveable relative to said basal end connecting portion, the tip end portion of said male luer occluding portion can be forwardly and backwardly moved relative to the tip end opening by rotating said basal end connecting portion in the axial direction relative to said tip end supporting portion while said internal thread portion is helically engaged with said external thread portion.

5. The male luer connector in accordance claim 1, wherein said displacement mechanism is configured such that said basal end connecting portion is rotatable in the axial direction relative to said tip end supporting portion, as well as, the rear end side portion of said male luer occluding portion is fixed to the predetermined portion of said basal end connecting portion, in which the tip end portion of said male luer occluding portion can be forwardly and backwardly moved relative to the tip end opening by moving said tip end supporting portion in the axis direction relative to said basal end connecting portion.

6. The male luer connector in accordance with claim 1, wherein said displacement mechanism is configured such that said basal end connecting portion is rotatable in the axial direction relative to said tip end supporting portion, an external thread portion is provided on the outer peripheral surface of said basal end connecting portion and an internal thread portion that can be helically engaged with said external thread portion of said basal end connecting portion is provided on the inner peripheral surface of said tip end supporting portion, the rear end side portion of said male luer occluding portion is secured to the predetermined portion of said basal end connecting portion, in which the tip end portion of said male luer occluding portion can be forwardly and backwardly moved relative to the tip end opening of said male luer part by rotating said basal end connecting portion about the axis relative to said tip end supporting portion.

7. The male luer connector in accordance with claim 1, wherein a thread portion to be engaged is provided to the outer peripheral surface of said female luer connector, a lock ring provided with an engagement thread portion that can be engaged with said thread portion to be engaged on the inner peripheral surface is mounted to the outer periphery side of said tip end supporting portion so as to be rotatable in the axial direction to helically engage said engagement portion with said thread portion to be engaged whereby said male luer connector can be connected to said female luer connector.

* * * * *